United States Patent [19]
Oreper et al.

[11] Patent Number: 5,756,904
[45] Date of Patent: May 26, 1998

[54] PRESSURE RESPONSIVE SENSOR HAVING CONTROLLED SCANNING SPEED

[75] Inventors: Boris Oreper, Newton; Paul Howard, Somerville, both of Mass.

[73] Assignee: Tekscan, Inc., Boston, Mass.

[21] Appl. No.: 706,409

[22] Filed: Aug. 30, 1996

[51] Int. Cl.⁶ .............................. G01L 15/00; G01L 9/06
[52] U.S. Cl. ........................................ 73/862.046; 73/721
[58] Field of Search ............................... 73/1.59, 1.15, 73/862.046, 721, 862.628

[56] References Cited

U.S. PATENT DOCUMENTS

| | | | |
|---|---|---|---|
| 4,442,716 | 4/1984 | Coe et al. | 73/721 X |
| 4,771,638 | 9/1988 | Sugiyama et al. | 73/721 |
| 4,856,993 | 8/1989 | Maness et al. | 433/68 |
| 5,010,774 | 4/1991 | Kikuo et al. | 73/862.046 |
| 5,237,879 | 8/1993 | Speeter | 73/862.041 |
| 5,505,072 | 4/1996 | Oreper | 73/4 R |

FOREIGN PATENT DOCUMENTS

| | | | |
|---|---|---|---|
| 142430 | 11/1981 | Japan | 73/862.046 |
| 102127 | 5/1987 | Japan | 73/862.046 |
| 32138 | 2/1989 | Japan | 73/862.046 |
| 2115555 | 9/1983 | United Kingdom | 73/862.046 |

*Primary Examiner*—Thomas P. Noland
*Attorney, Agent, or Firm*—Wolf, Greenfield & Sacks, P.C.

[57] ABSTRACT

A circuit and various sensor arrays are provided which facilitate the scanning of an array of pressure responsive points at higher speed than is possible with currently available circuits and sensor arrays and also provides greater flexibility in selecting scanning speed and in making a tradeoff between scanning speed and resolution. These objectives are achieved by providing a sensor array having T sets of drive electrodes, with pressure points in a predetermined pattern intersected by drive electrodes of each set and a sense electrode for each pressure point of a set. A test signal is applied simultaneously to the drive electrodes of each set, with a different test signal being applied to each set, each test signal flowing through a drive electrode to which the test signal is applied, and through pressure points intersected by such drive electrode for which the resistance is in a lowered resistance state, to the sense electrode intersecting the point, and through sensor output lines to which the sense electrodes are selectively connected. The sense electrodes may be selectively connected to an output circuit which may for example provide a separate A/D converter for each sensor output line or may multiplex the sensor output lines to a single A/D converter. For one embodiment of the invention, T=1 so that a single test pulse may be applied simultaneously to all of the pressure points of the sensor array. Various techniques are also provided for enhancing resolution in areas of interest while sacrificing resolution in areas which are not of interest so as to permit higher speed scanning to be performed without significant sacrifice in resolution.

20 Claims, 10 Drawing Sheets

5,756,904

1

PRESSURE RESPONSIVE SENSOR HAVING CONTROLLED SCANNING SPEED

FIELD OF THE INVENTION

This invention relates to pressure sensitive arrays and circuits for the scanning thereof and more particularly to such sensor arrays and circuits which scan both faster and with greater flexibility in achievable scanning rate than previous circuits.

BACKGROUND OF THE INVENTION

U.S. Pat. No. 4,856,993 (hereinafter the '993 Patent) and U.S. Pat. No. 5,505,072 (hereinafter the 072 Patent), both of which patents are assigned to the assignee of the current application, described variable resistance pressure sensing arrays and circuits for scanning such arrays. Such arrays may, for example, be used as a contact sensor for dental occlusion, to detect foot pressure in a shoe, to detect pressure distribution on a gasket, and in numerous other applications in industry, research, military and the like where information on pressure or force distribution over a defined area is required. While the circuits/sensor arrays of these patents do an excellent job in performing the pressure sensor and scanning function, one limitation of these circuits is that they are capable of operating at only a single scanning speed for a given scanner. This speed is a function of a number of things including settling times for the sensors and operational amplifiers (op amps) utilized and settling time for the analog-to-digital (A/D) converters utilized. Assuming the combined settling times of the sensor and op amp are approximately 1.0 μs and that the settling time for the A/D converter is approximately 1 μs, the time for each test pulse applied to a 16×16 sampling circuit would be approximately 17 μs. Since sixteen test pulses would be required to fully sample such array (i.e., one test pulse for each drive electrode), the total sample time for each frame (i.e., for a sampling of the entire array) would be approximately 272 μs.

The prior art teaches two ways in which this scan time can be reduced. One way, suggested in the patents, is to utilize a separate A/D converter for each output line rather than multiplexing the output lines through a single A/D converter. For a 16×16 array, this reduces the sampling time to approximately 32 μs, a significant improvement. However, since A/D converters are relatively expensive components, the requirement for sixteen A/D converters may make the circuit too expensive for many applications.

A second potential solution is taught in U.S. Pat. No. 5,237,879 which utilizes a somewhat different circuit to scan pressure points. In this circuit, the problem is dealt with by sacrificing resolution so that, instead for example of having a 16×16 array for a given area, only a 4×4 array would be utilized for this area. This results in a scan time of approximately 72 μs, with ¼ the resolution of the 16×16 array. Because of the design of this circuit, it is not possible to increase this speed by using multiple A/D converters. Thus, each of these prior art solutions achieves higher speed operation either by sacrificing resolution and/or by significantly increasing costs, but neither of these solutions has been able to reduce scan time below approximately 32 μs for an area normally covered by a 16×16 array.

Further, while 16×16 arrays have been discussed in the examples above, arrays used in many applications are frequently much larger, an array of 256×256 not being uncommon. Scanning time for such large arrays can be in the millisecond range, which may not be acceptable in some

2 applications such as crash tests for automotive and other industries, and the cost of providing a separate A/D converter at each of the 256 circuit outputs could be prohibitively expensive. Therefore, a solution which permits an optimum tradeoff between scanning speed and resolution to be achieved for a given sensor array is desirable. In order to maximize flexibility while minimizing cost, it is desirable that such flexibility be achievable by modifying only the sensor array itself, and not the underlying circuitry.

SUMMARY OF THE INVENTION

In accordance with the above, this invention provides a circuit for facilitating the higher speed scanning of an array of pressure responsive sensor points and a sensor array for use in such circuit. Each sensor or pressure point is at an intersection of a selected drive electrode and a selected sense electrode. In the sensor array, there is pressure sensitive resistance between the electrodes intersecting at each pressure point. The circuit includes a test-signal generator which generates test signals during each scan of the array. A sensor array is also provided having sets of drive electrodes, each of which sets has at least one drive electrode, and at least one of which sets has a plurality of drive electrodes, there being pressure points in a predetermined pattern intersected by the drive electrodes of each set. A set of drive electrodes may be defined by interconnecting the drive electrodes of the set or by programmably controlling the applications of test pulses to the drive electrodes so that a test pulse is simultaneously applied to all the drive electrodes of the set. The array also has a sense electrode for each pressure point of a set. A test signal is applied simultaneously to the drive electrodes of each set with a different test signal being applied to each set, each test signal flowing through a drive electrode to which the test signal is applied, and through sensor points intersected by such drive electrode for which resistance is in a lowered resistance state to the sense electrode intersecting the point. Finally, the array has sensor output lines to which the sensor electrodes are selectively connected. The circuit also includes an output circuit to which the sensor output lines are selectively connected.

For preferred embodiments, the number of the pressure points for each set is a constant S, there being S sensor output lines from the sensor array. The S pressure points for each set may be divided equally among the drive electrodes of the set or the S pressure points of each set may be divided so that some electrodes intersect more pressure points than others, resolution being higher in the area of the electrodes intersecting more pressure points. Similarly, each of the sets may have the same number of drive electrodes or some of the sets may have more drive electrodes than others, resolution being higher in the areas of the sets having fewer drive electrodes.

The output circuit may include a separate A/D converter for each sensor output line through which test signals at the corresponding sense electrodes are applied or may include a single A/D converter to which test signals on a sensor output lines are applied and a multiplexer for selectively applying test signals on the sensor output lines to the A/D converter. Where T=1, a single test signal is applied to all sensor points simultaneously. For some embodiments, at least one selected sense electrode may be connected to at least two different sensor output lines, with the output circuit including a scanner for sequentially sampling the sensor output lines in a manner such that the sensor output lines connected to a sensor electrode are sampled at spaced time intervals.

A sensor array for use in the scanning circuit includes T sets of drive electrodes, each of which sets has at least one drive electrode and at least one of which sets has a plurality of drive electrodes, there being pressure points in a predetermined pattern intersected by the drive electrodes of each set. A sense electrode is also provided for each pressure point of a set. A test signal is applied simultaneously to the drive electrodes of each set, with a different test signal being applied to each set. The test signal flows through a drive electrode to which the test signal is applied, and through pressure points intersected by such drive electrode for which the resistance is in a lowered resistance state, to a sense electrode intersecting the point. An input through which a test signal may be applied is provided for each of the T sets of interconnected drive electrodes and sensor output lines are provided to which the sense electrodes are selectively connected. As indicated earlier, the number of the pressure points for each set is preferably a constant S, with there being S sensor output lines from the sensor array. The S pressure points for each set may be divided equally among the drive electrodes of the set or the S pressure points of each set may be divided so that some electrodes intersect more pressure points than others, resolution being higher in the area of the electrodes intersecting more pressure points. Similarly, each set of electrodes may have the same number of drive electrode or some sets may have more drive electrodes than others, resolution being higher in the areas of the sets having fewer drive electrodes.

A more flexible circuit may also be provided wherein at least two sensor arrays of the type discussed above are stacked adjacent each other between surfaces for which differential pressure is to be measured. For such sensors, the speed at which sensing can be performed by the circuit using a given sensor array is inversely proportional to the value T for the array. In such circuit, a means is provided for selectively connecting one of the sensor arrays into the circuit depending on the desired sensing speed. The circuit may also include a test-pulse generator for applying a separate test pulse to the input for each of the T sets of interconnected drive electrodes and an output circuit to which the outputs from the sense electrodes are connected.

The foregoing and other objects, features and advantages of the invention will be apparent from the following more particular description of preferred embodiments of the invention as illustrated in the accompanying drawings.

IN THE DRAWINGS

Figure 7A:
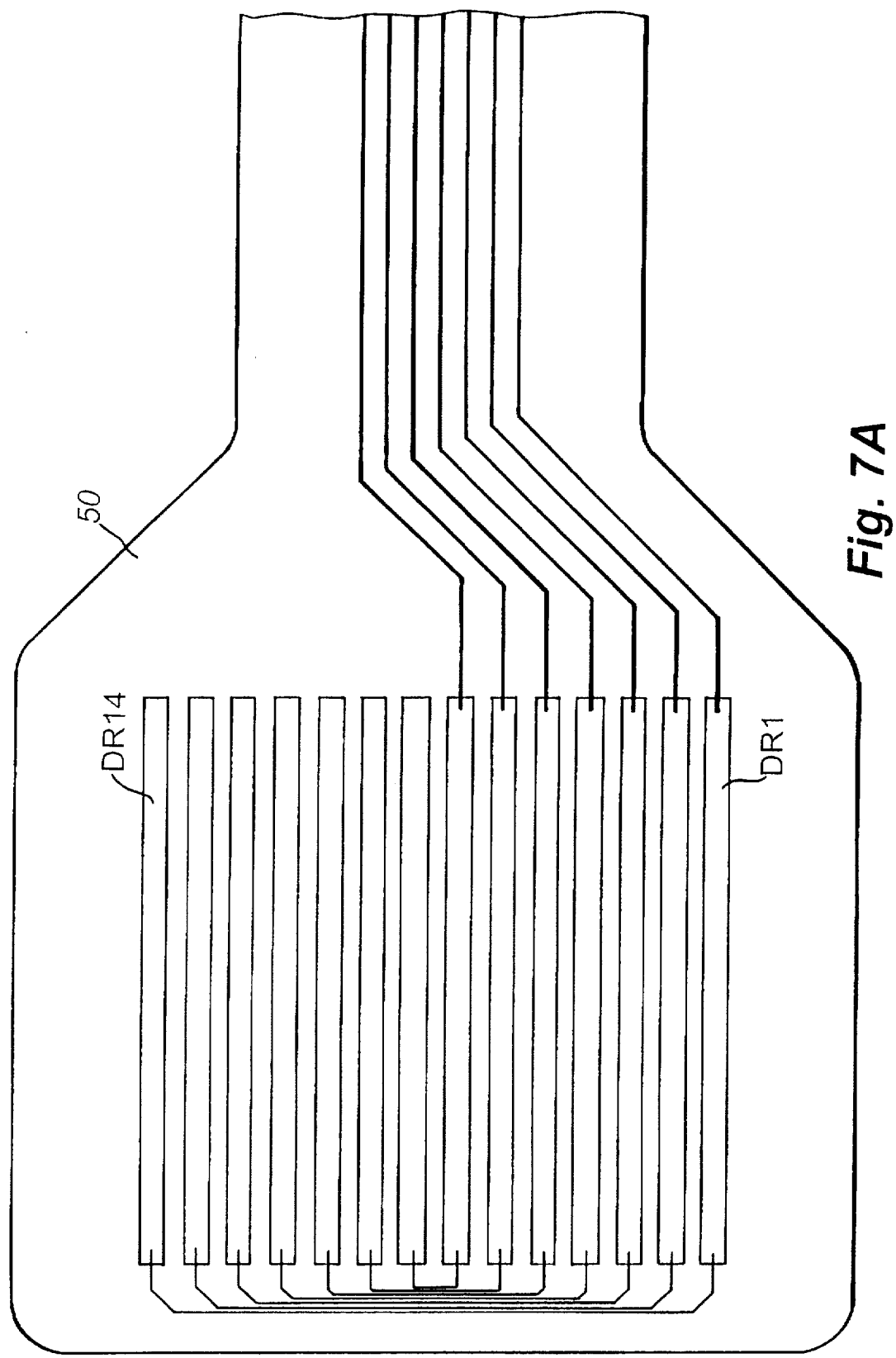
Figure 7B:
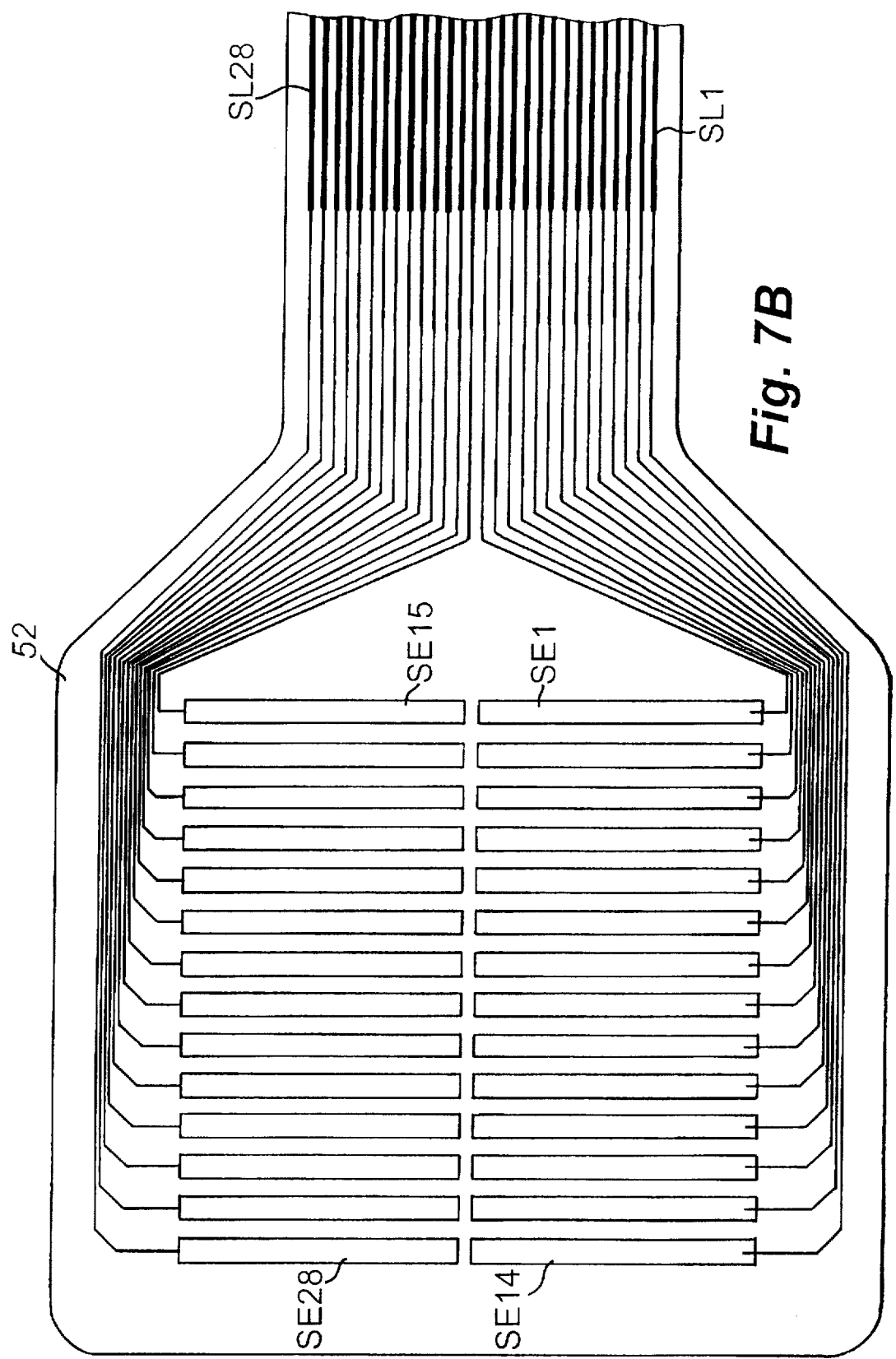

FIGS. 7A and 7B, when combined, illustrate still another alternative sensor array in accordance with the teachings of this invention.

Figure 8:
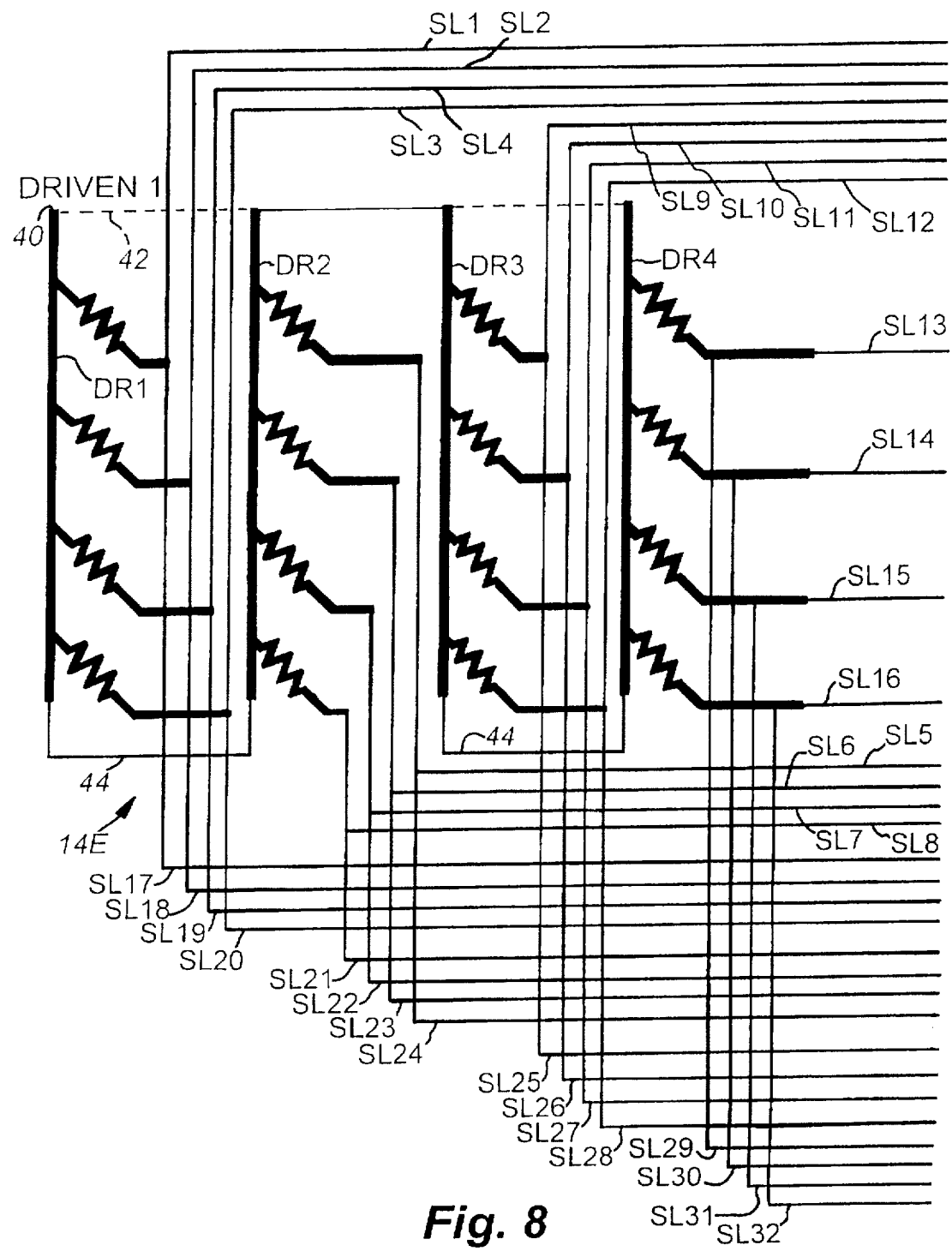

FIG. 8 is a schematic diagram of still another alternative sensor array.

Figure 9:
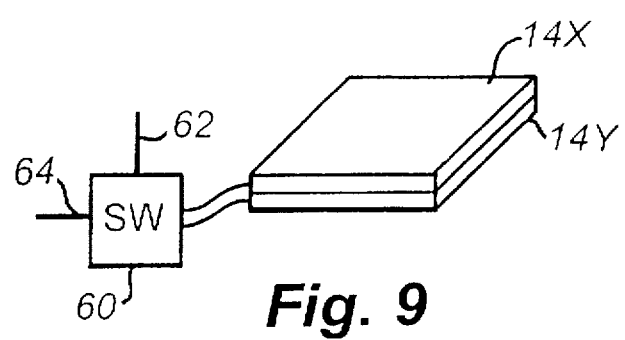

FIG. 9 is a semi-block schematic diagram of an illustrative switched sensor array stack.

DETAILED DESCRIPTION

Figure 1:
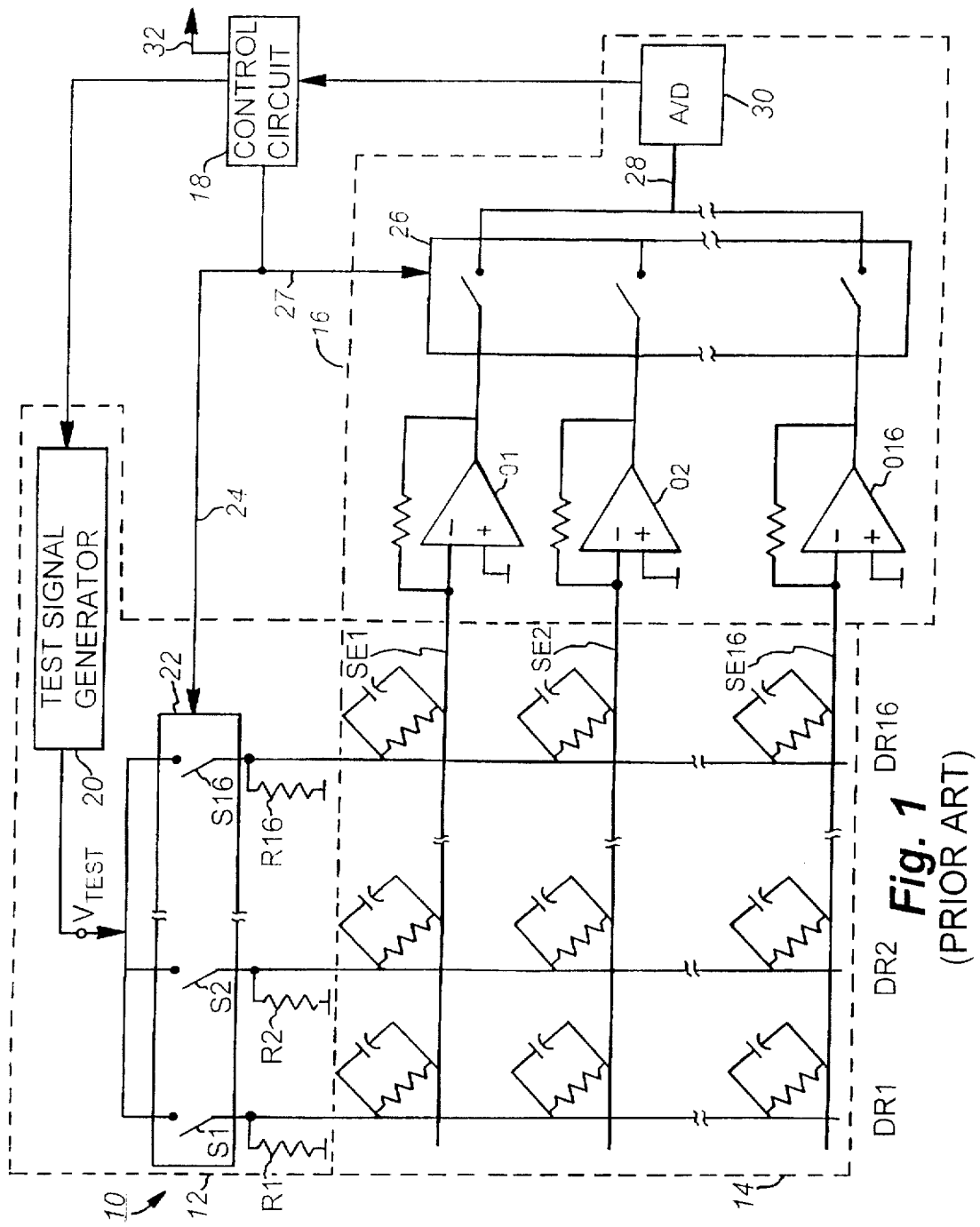
FIG. 1 is a simplified semi-block schematic diagram of a prior art scanning circuit for a pressure responsive sensor array of the type shown in the '072 patent.

FIG. 1 is a simplified semi-block schematic diagram of a prior art pressure responsive sensor scanning circuit of, for example, the type shown in beforemention U.S. Pat. No. 5,505,072. The circuit 10 has four major elements, namely a test signal generating input circuit 12, a sensor array circuit 14, an output circuit 16 and a control circuit 18. Input circuit 12 includes a test signal generator 20, the output from which is applied to a multiplexer switch 22 which, under control of a signal on line 24 from control 18, causes the test signal to be applied to a selected one of the drive electrodes DR1–DR16 of sensor array 14. There are also a plurality of output or sense electrodes SE1–SE16 in sensor array 14, the drive and sense electrodes being at substantially right angles to each other so that each drive electrode intersects at one point with each sense electrode. For preferred embodiments, a pressure sensitive resistive ink is positioned between the electrodes at each junction, the resistance of such ink being relatively high so as to substantially prevent current flow between the intersecting electrodes at points where low pressure is being applied to array 14, and the resistance decreasing as the pressure at a junction point of electrodes is increased, so as to permit increasing current flow between the electrodes. The output current at a point being sampled is therefore a measure of the pressure applied at the point. The sensitivity of the sensor may be adjusted in a manner discussed in the before mentioned '072 patent depending on the anticipated range of applied pressures. The circuit has trace capacitances at the various junctions or pressure points which are also illustrated in FIG. 1. Since the discharge time for such stray capacitances could be in the order of 1 millisecond per test pulse, the circuit of FIG. 1 also includes bypass resistors R1–R16 in parallel with each of the drive electrodes, which resistors are of relatively low value, through which the trace capacitances for a sensor or pressure point may rapidly discharge, thereby reducing the settling time for the circuit between scans to as little as one microsecond. This mechanism is described in greater detail in the before mentioned '072 patent.

A test signal passing to a sense electrode SE1–SE16 is applied through a corresponding operational amplifier circuit 01–016 of output circuit 16 to a multiplexer switch 26 which scans the outputs from the operational amplifiers under control of signals on line 27 from control circuit 18. The single output line 28 from multiplexer 26 is digitized in A/D converter 30, and the resulting digital output applied to control circuit 18. Control circuit 18 utilizes this output to generate an output 32 from the circuit 10, and may also use this information in conjunction with other information in its programming to control test signal generator 20. The circuit 10 and the operation thereof are described in greater detail in the '072 patent and such description is incorporated herein by reference.

However, with the circuit shown in FIG. 1, the settling time for the sensor array, and in particular for the discharge of stray capacitances through resistors R1–R16, is approximately 0.05 μs for each drive electrode and the settling time for each operational amplifier 01–016 is approximately 1 μs. The settling time for the A/D converter 30 is approximately 1 μs. Therefore, the scan of a single line DR1–DR16 takes a little over 17 μs, resulting in a scan time for the 16×16 array shown in FIG. 1 of approximately 272 μs. For larger arrays, for example a 64×64 array or a 256×256 array, the scan time is significantly longer. While these scan times are acceptable in many applications, there are applications where shorter scan times are required.

Figure 2:
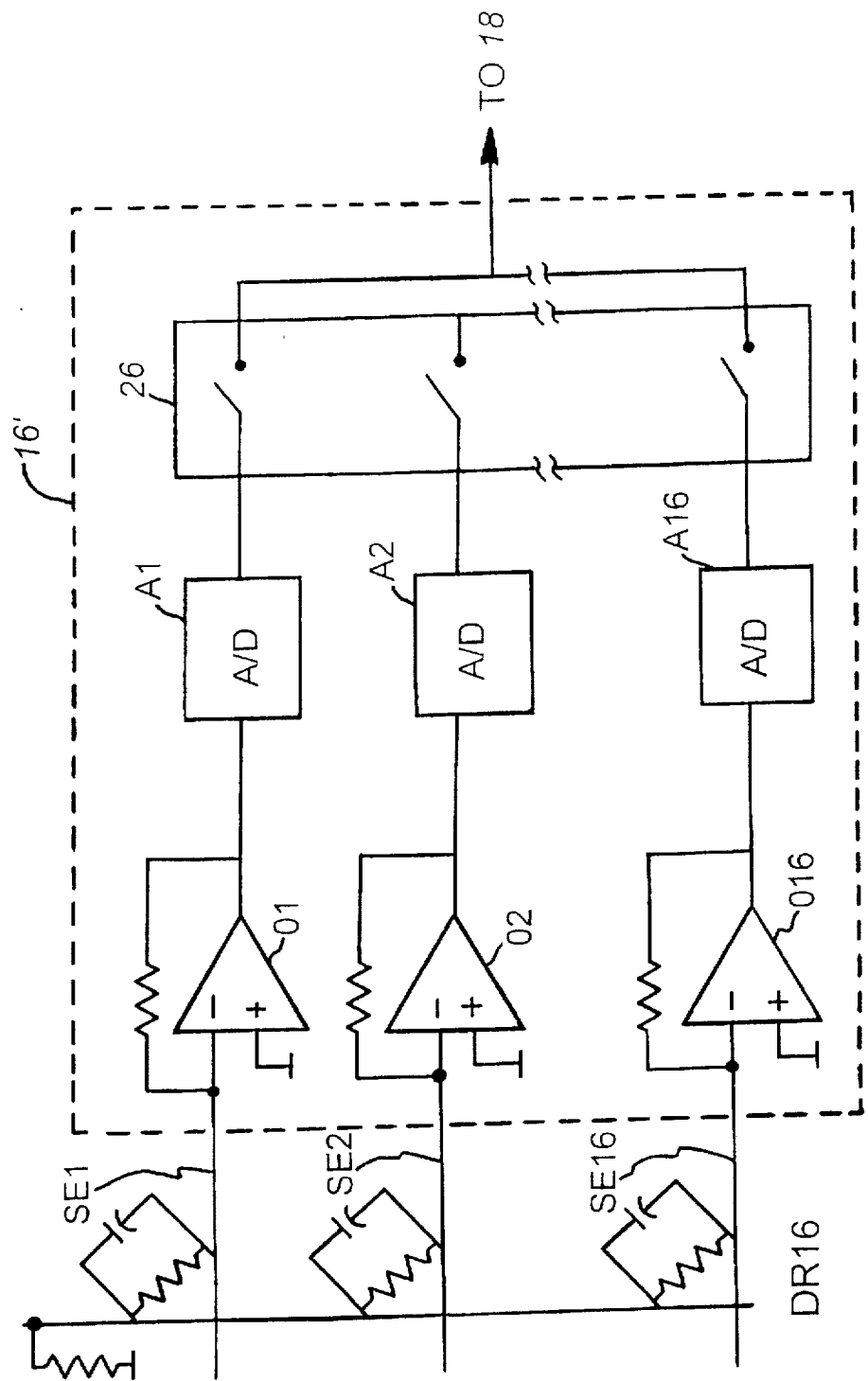
FIG. 2 is a semi-block schematic diagram of an alternative output circuit for use in either the prior art scanning circuit shown in FIG. 1 or with the circuit of this invention.

FIG. 2 shows one prior art solution for reducing the time to complete a scan for sensor array 14 which involves substituting an output circuit 16' which has a separate A/D converter A1–A16 for the output of each op amp 01–016, with output multiplexer 26 being at the output of the A/D converters rather than at the output of the op amps. Since the major time for each scan previously was the settling time of the A/D converter, the arrangement of FIG. 2 permits the time required for the application of a test signal to each drive electrode DR1–DR16 to be reduced to a little over 2 µs, so that the total time for a scan of the sensor shown in FIG. 1 is reduced to approximately 33 µs. However, A/D converters A1–A16 are relatively expensive items and therefore using a separate A/D converter for each sensor electrode significantly increases the cost of the circuit 10, particularly for large sensors. Further, even 33 µs may not be fast enough for some applications.

Therefore, a need exists to permit further reductions in scan time, possibly with some reduction in resolution, without requiring significant changes in the circuit 10 of FIG. 1. In particular, the least expensive portion of this circuit is sensor 14, which is typically formed of two printed circuit layers, one for each set of electrodes, which may be formed on a suitable backing such as Mylar, with resistive ink being suitably coated over the electrodes and the two layers then laminated. In many applications, such as, for example, to detect dental occlusion or in certain industrial applications, the sensors are disposable and are replaced after each usage. Therefore, it would be desirable if a sensor could be provided which could be substituted for the sensor 14 in the circuit of FIG. 1 or FIG. 2 in applications where higher speed were required, without requiring any other change in the circuit except for a reprogramming of control circuit 18.

From the previous discussion it is apparent that, while the time for scanning a single one of the drive electrodes DR1–DR16 is not great, each additional electrode which needs to be scanned, or in other words each additional test pulse which is applied to the sensor array, results in a significant increase in scan time. Therefore, scan time can be reduced by designing the circuit 10 so that each test pulse is applied to a selected plurality of the drive electrodes DR1–DR16, the total number of test pulses for a scan of the array can be reduced. For example, if each test pulse were applied to two drive electrodes rather than a single drive electrode, so that only half as many test pulses were required, the scan time could be reduced by roughly 50%. In the extreme case where only a single test pulse is simultaneously applied to all of the drive electrodes, the scan time can be reduced to substantially the times previously indicated for the scanning of a single drive electrode. However, such increase in speed is obtained at the cost of resolution.

Figure 3:
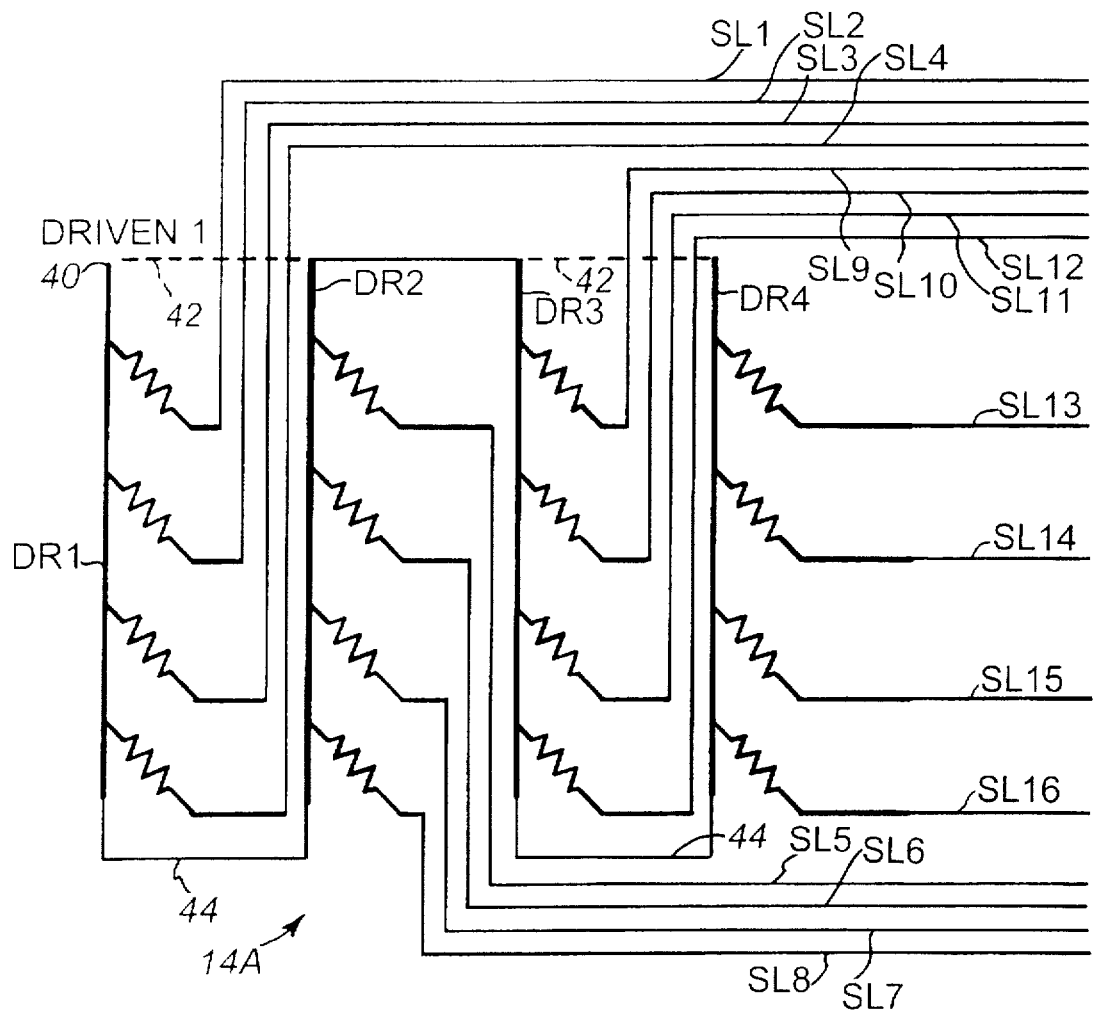
FIG. 3 is a schematic diagram of a sensor array suitable for use in the circuit of FIG. 1 in place of the sensor array shown, which sensor array is in accordance with the teachings of this invention.

Referring for example to FIG. 3, a sensor array 14A is shown which could be utilized in FIG. 1 or in FIG. 2 in lieu of the sensor array 14 shown. The array has four drive electrodes DR1–DR4, each of which has four sensor pressure points. Each sensor point is also defined by a sensor electrode SE1–SE16 which is connected to a corresponding separate sensor output line SL1–SL16, each of which may be connected as an input to an op amp 01–016 as shown in FIGS. 1 and 2. The drive electrodes may be connected in series as shown in FIG. 3 so that a single test pulse is applied simultaneously to the four drive electrodes, the test signal being applied, for example, at point 40 through, for example, a closed switch So in multiplexer 22. The connection at point 40 could be the only connection between the multiplexer 22 and sensor array 14A. As illustrated by the dotted lines 42, the drive electrodes DR1–DR4 could also be connected in parallel, in which case the connecting lines 44 at the bottom of the array would be eliminated. It is also possible for lines 42 and 44 to be eliminated, with selected switches S1–S16 of switch 22 being closed to simultaneously apply a test pulse to the desired drive lines.

As discussed above, a circuit utilizing the array shown in FIG. 3 requires roughly 1/16 the scan time of the circuit shown in FIG. 1 and would therefore have a scan time of, for example, a little over 17 µs if a single A/D converter is utilized as shown in FIG. 1 and a scan time of only a little over 2 µus if multiple A/D converters are utilized as shown in FIG. 2. However, this reduction in scan time is accompanied by a corresponding 16-fold reduction in resolution, the circuit having only 16 sensor points rather than 256 sensor points. In some applications, such a reduction in the number of sensor points may be acceptable in order to achieve higher speed sensing. However, where higher resolution is required than can be achieved utilizing the sensor shown in FIG. 3, several options are available.

Figure 4:
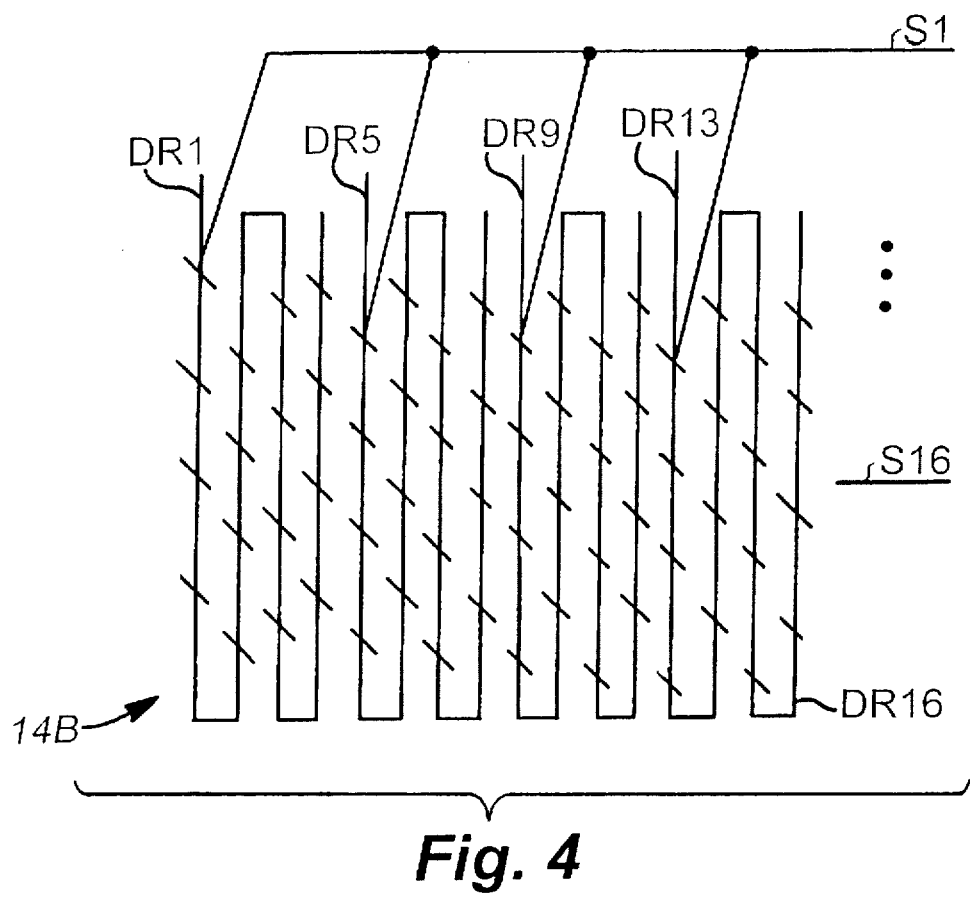
FIGS. 4, 5 and 6 are schematic diagrams of three alternative sensor arrays in accordance with the teachings of this invention.

FIG. 4 illustrates one such option wherein, instead of having only a single test pulse applied to a single drive electrode set, the 16 drive electrodes DR1–DR16 of the array 14B are shown interconnected into four sets of drive electrodes, with four drive electrodes in each set. However, each drive electrode has only four sensor points, rather than 16 sensor points as for the embodiment of FIG. 1, resulting in 16 sense electrodes and 16 outputs for each drive electrode set. Test pulses are sequentially applied to drive electrodes DR1, DR5, DR9 and DR13. Attentively, with the drive electrodes not interconnected, the first test pulse would be applied to drive electrodes DR1, DR2, DR3 and DR4, the second test pulse to drive electrodes DR5, DR6, DR7, DR8, etc. Corresponding sense electrodes for the drive electrode sets are interconnected by a sense line SL1–SL16. For simplicity of illustration, only the interconnections for the output sense line SL1 are shown in FIG. 4, but similar connections would be made for the other sensor electrodes to output sense lines SL2–SL16. The embodiment of FIG. 4 represents a compromise in that it is four times as fast, but has only one quarter the resolution of the sensor shown in FIG. 1, while being one quarter as fast but having four times the resolution of the embodiment shown in FIG. 3.

Figure 5:
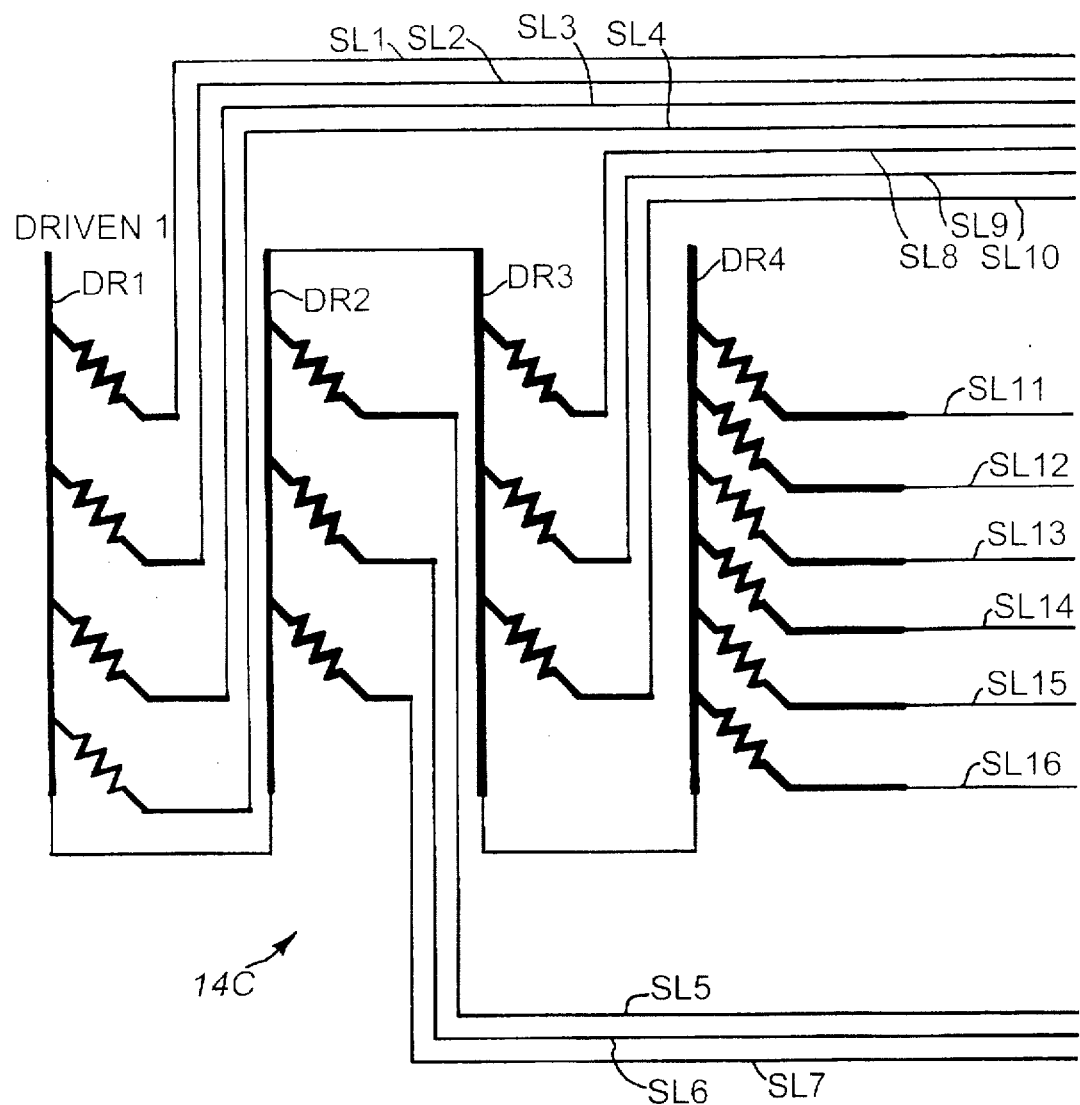

FIG. 5 shows another alternative embodiment (14C) of the invention which, while having the same speed and overall resolution as that shown in FIG. 1, takes advantage of the fact that the resolution requirements are not uniform over the surface being scanned. In particular, it is assumed for this embodiment that higher resolution is required on the left and right sides of the area than in the center, with the highest resolution being required on the right side. Therefore, there are four sensor points for drive electrode DR1 and six sensor points for drive electrode DR4, while drive electrodes DR2 and DR3 have only three sensor points each. In some applications, it may even be possible to place seven or eight sensor points on drive electrodes DR1 and DR4, with one or zero sensor points on the remaining drive electrodes where there is little or no interest in what is happening at these points in the array. Thus, sensing speed may be enhanced by sacrificing resolution in areas where resolution is not of concern, while maintaining resolution in areas where such resolution is of concern.

Figure 6:
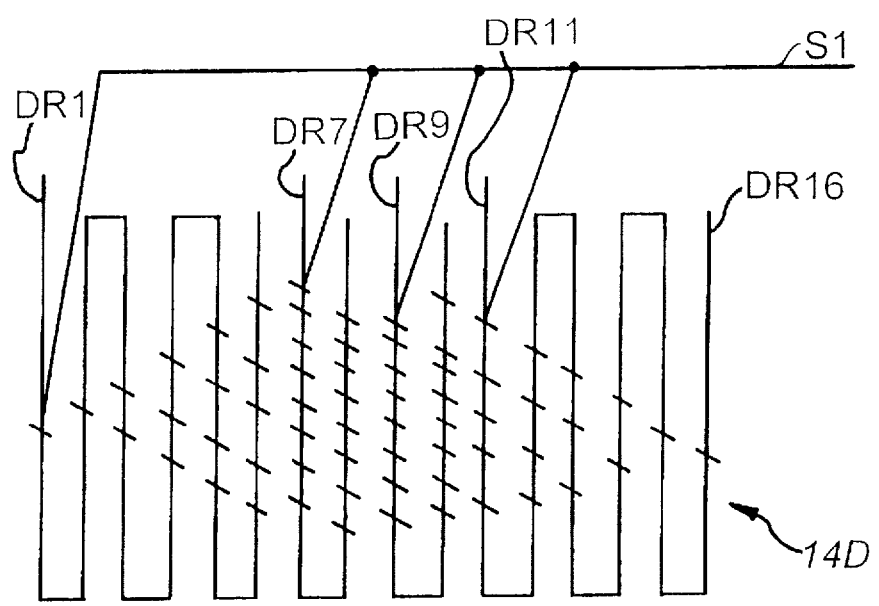

FIG. 6 shows another way in which this objective may be achieved. In this figure, higher resolution is required in the center of the array and less resolution is required as one moves away from the center. The sixteen drive electrodes are interconnected into four sets of drive electrodes, but there are six drive electrodes in each of the outer sets and only two drive electrodes in each of the middle sets. Test pulses are sequentially applied to drive electrodes DR1, DR7, DR9 and DR11. Since each set can have only a total of sixteen sense points, each drive electrode in the center two sets intersects eight sense points, while the drive electrodes in the two outer sets intersect a decreasing number of sense points as they are increasingly spaced from the center. Thus, drive electrodes DR1, DR2, DR15 and DR16 each pass through only a single sense point, with drive electrodes DR3 and DR14 passing through two sense points each, drive electrodes DR4 and DR13 passing through three sense points each, drive electrodes DR5 and DR12 passing through four sense points each and drive electrodes DR6 and DR11 passing through five sense points each. The scanning time and resolution for the sensor array shown in FIG. 6 is the same as that for the sensor array shown in FIG. 4; however, the resolution near the center of the array is increased to be ½ that of the array shown in FIG. 1, while it is only 1/16 that shown in FIG. 1 at the left and right of the array. Other configurations can also be designed to meet diverse speed and resolution requirements and diverse interconnect requirements of the circuits in which the sensor arrays are utilized.

FIGS. 7A and 7B illustrate a drive substrate 50 and a sensor substrate 52 which may be interconnected to form a sensor array having seven input or drive electrodes to which test pulses may be applied and 28 sensor output lines, thus providing 196 sensor points. The drive electrodes DR1 and DR14 are interconnected to have the same test pulse applied thereto, as are the drive electrodes DR2 and DR13, etc. A separate sensor output line SL1–SL28 is provided for each of the 28 sensor electrodes. The circuit of FIGS. 7A and 7B illustrates that the number of drive electrodes and the number of sensor electrodes need not be the same, and further illustrates the situation where resolution is reduced and scan time improved by 50%.

FIG. 8 shows another embodiment of the invention which is similar to FIG. 3 and has only a single test pulse applied to the four drive electrodes DR1–DR4. However, instead of having only sixteen sensor output lines SL1–SL16, the sensor array 14E has thirty-two sensor output lines SL1–SL32, with each sensor point electrode being connected to two spaced apart sensor output lines. The scanning circuit scans the sensor output lines in order, starting with sensor output line SL1 and finishing with sensor output line SL32. Therefore, during a single test pulse, each pressure point is sampled twice at time intervals which are separated by some number of micro seconds. The same objective could be achieved by maintaining the test pulse and scanning sensor output lines SL1–SL16 in sequence twice. However, assuming a separate op amp and a separate A/D converter is used for each of the sensor output lines, the circuit shown in FIG. 8, with 32 sensor output lines, could provide two complete scans of the array in a little over 2 µs, or a little over 1 µs per scan.

While typically only a single sensor array 14 would be utilized with a circuit 10, applications are possible where it may be desirable to be able to operate either in a high-speed or high-resolution mode and to have the flexibility to switch between the two. FIG. 9 illustrates one way in which this might be accomplished. Referring to FIG. 9, sensors 14X and 14Y are stacked with sensor 14X, for example, being a lower speed high resolution sensor such as that shown in FIG. 1 and sensor 14Y being a higher speed, lower resolution array such as that shown in FIG. 3 or FIG. 4. The arrays 14X and 14Y are connected through a switch 60, receiving a control signal on a line 62 from, for example, control circuit 18, to a cable 64 leading to the remainder of circuit 10. Three or more different sensor arrays could be stacked and switched if there was a requirement for such flexibility.

In FIGS. 3–8, the sense lines have been shown as being brought out in parallel from various points around the array. However, there may be applications, particularly for large arrays with many sense lines being outputted, where there is not room on the array to bring out all of the sense lines without having some sense lines pass through a sense point. For arrays where this may be a problem, the technique taught in U.S. Pat. No. 5,033,291 may be utilized to insulate the sense electrodes from the sense points. In this patent, the sense electrodes or sense output lines are formed on an insulating layer overlying the sensor array, with each electrode being connected to the corresponding sense point or with sense output lines being connected to each sense electrode by a plated-through hole or other suitable interconnect formed through the insulating layer.

While the invention has been described above with respect to an illustrative circuit 10, and various illustrative sensor arrays and output circuits have been shown, the circuit utilized in practicing the invention may vary with application and the sensor array utilized will also vary with application and with the required sensing speed and resolution. For example, instead of interconnecting the drive electrodes of each set as shown and described above, the objective of applying a test pulse simultaneously to all of the drive electrodes of a set could be achieved as also discussed in switch 22 under control of control circuit 18. While a suitable programmable switch would currently be more expensive than the technique previously described, in some applications, this mode of operations might be preferred. Thus, the embodiments shown are for purposes of illustration only, and the foregoing and other changes in form and detail may be made in practicing the invention by those skilled in the art while still remaining within the spirit and scope of the invention, which is defined by the appended claims.

What is claimed is:

1. A circuit for scanning an array of pressure responsive pressure points, each of which points is defined by the intersection of a selected drive electrode and a selected sense electrode, there being a pressure sensitive resistance between the electrodes intersecting at each of said points, the circuit comprising:

a test signal generator adapted to generate T test signals during each scan of said array;

a sensor array having T sets of drive electrodes, each of which sets has at least one drive electrode, and at least one of which sets has a plurality of drive electrodes, there being pressure points in a predetermined pattern intersected by the drive electrodes of each set, a sense electrode for each pressure point of a set, a test signal being applied simultaneously to the drive electrodes of each set, and a different test signal being applied to each set, each test signal flowing through a drive electrode to which the test signal is applied, and through pressure points intersected by such drive electrode for which the resistance is in a lowered resistance state, to the sense electrode intersecting the point, and sensor output lines to which said sense electrodes are selectively connected; and an output circuit to which said sensor output lines are selectively connected.

2. A circuit as claimed in claim 1 wherein the number of the pressure points for each set is a constant S, there being S sensor output lines from the sensor array.

3. A circuit as claimed in claim 2 wherein the S pressure points for each set are divided equally among the drive electrodes of the set.

4. A circuit as claimed in claim 2 wherein each of the sets has the same number of drive electrodes.

5. A circuit as claimed in claim 2 wherein the S pressure points of each set are divided so that some electrodes intersect more pressure points than others, resolution being higher in the area of the electrodes intersecting more pressure points.

6. A circuit as claimed in claim 2 wherein some of said sets have fewer drive electrodes than others, resolution being higher in the areas of the sets having fewer drive electrodes.

7. A circuit as claimed in claim 2 wherein said output circuit includes a separate A/D converter for each sensor output line through which test signals from the corresponding electrodes are applied.

8. A circuit as claimed in claim 2 wherein said output circuit includes a single A/D converter through which test signals on said sensor output lines are applied, and a multiplexer for selectively applying test signals on the sensor output lines to the A/D converter.

9. A circuit as claimed in claim 1 wherein T=1 so that there is only one set containing all drive electrodes, the single test signal therefore being applied to all sensor points simultaneously.

10. A circuit as claimed in claim 1 wherein at least selected sense electrodes are connected to at least two different sensor output lines, and wherein said output circuit includes a scanner for sequentially sampling said sensor output lines in a manner such that the sensor output lines connected to a sense electrode are sampled at spaced time intervals.

11. A sensor array for use in a circuit for scanning an array of pressure responsive sensor points by applying at least one test signal through the sensor array comprising:

T sets of drive electrodes, each of which sets has at least one drive electrode, and at least one of which sets has a plurality of drive electrodes, there being pressure points in a predetermined pattern intersected by the drive electrodes of each set, a sense electrode for each pressure point of a set, a test signal applied to a set of drive electrodes flowing through a drive electrode, and through pressure points intersected by such drive electrode for which the resistance is in a lowered resistance state, to a sense electrode at the point;

an input through which a test pulse may be applied to each of said T sets of interconnected drive electrodes; and sensor output lines to which said sense electrode are selectively connected.

12. A sensor as claimed in claim 11 wherein the number of the pressure points for each set is a constant S, there being S sensor output lines from the sensor array.

13. A sensor as claimed in claim 12 wherein the S pressure points for each set are divided equally among the drive electrodes of the set.

14. A sensor as claimed in claim 12 wherein each of the sets has the same number of drive electrodes.

15. A sensor as claimed in claim 12 wherein the S pressure points of each set are divided so that some electrodes intersect more pressure points than others, resolution being higher in the area of the electrodes intersecting more pressure points.

16. A sensor as claimed in claim 12 wherein some of said sets have more drive electrodes than others, resolution being higher in the areas of the sets having fewer drive electrodes.

17. A sensor as claimed in claim 11 wherein T=1, all of the drive electrodes of the sensor array being connected to form a single set.

18. A sensor as claimed in claim 11 wherein at least selected sense electrodes are connected to at least two different sensor output lines.

19. A circuit for scanning an array of pressure responsive sensor points which includes at least two sensor arrays of claim 11 stacked adjacent each other and adapted to be placed between surfaces for which differential pressure is to be measured, the speed at which sensing can be performed by the circuit using a given sensor array being inversely proportional to the value T for the array, and further including means for connecting a selected one of said sensor arrays into the circuit depending on the desired sensing speed.

20. A circuit as claimed in claim 19 including a test pulse generator for applying a separate test pulse to the input for each of said T sets of interconnected drive electrodes, and an output circuit to which the outputs from said sense electrodes are connected.

\* \* \* \* \*